US00PP19205P2

(12) United States Plant Patent
Roberson

(10) Patent No.: US PP19,205 P2
(45) Date of Patent: Sep. 9, 2008

(54) ***HEMEROCALLIS* PLANT NAMED 'ROBDAYSTE'**

(50) Latin Name: *Hemerocallis hybrida*
Varietal Denomination: Robdayste

(76) Inventor: Robert J. Roberson, P.O. Box 210, Grain Valley, MO (US) 64029

( * ) Notice: Subject to any disclaimer, the term of this patent is extended or adjusted under 35 U.S.C. 154(b) by 0 days.

(21) Appl. No.: 11/879,106

(22) Filed: Jul. 15, 2007

(51) Int. Cl.
*A01H 5/00* (2006.01)

(52) U.S. Cl. ..... Plt./312

(58) Field of Classification Search ..... Plt./312
See application file for complete search history.

*Primary Examiner*—Wendy C. Haas
(74) *Attorney, Agent, or Firm*—C. A. Whealy

(57) ABSTRACT

A new and distinct cultivar of *Hemerocallis* plant named 'Robdayste', characterized by its compact, outwardly arching and clumping plant habit with upright flower scapes; freely flowering habit; pink-colored flowers with red purple-colored centers that are positioned above the foliage on strong scapes; and good garden performance.

2 Drawing Sheets

Botanical designation: *Hemerocallis hybrida.*
Cultivar denomination: 'Robdayste'.

BACKGROUND OF THE INVENTION

The present invention relates to a new and distinct cultivar of *Hemerocallis,* botanically known as *Hemerocallis hybrida* and hereinafter referred to by the name 'Robdayste'.

The new *Hemerocallis* is a product of a planned breeding program conducted by the Inventor in Grain Valley, Mo. The objective of the breeding program is to create new compact *Hemerocallis* cultivars with unique flower colors.

The new *Hemerocallis* originated from a cross-pollination made by the Inventor in July, 1998, in Grain Valley, Mo., of the *Hemerocallis hybrida* cultivar Janice Brown, not patented, as the female, or seed, parent with a proprietary selection of *Hemerocallis hybrida,* not patented, as the male, or pollen, parent. The new *Hemerocallis* was discovered and selected by the Inventor as a flowering plant within the progeny of the stated cross-pollination in a controlled environment in Grain Valley, Mo. in July, 2000.

Asexual reproduction of the new *Hemerocallis* by divisions in a controlled environment in Grain Valley, Mo. since September, 2002, has shown that the unique features of this new *Hemerocallis* are stable and reproduced true to type in successive generations.

SUMMARY OF THE INVENTION

The cultivar Robdayste has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Robdayste'. These characteristics in combination distinguish 'Robdayste' as a new and distinct cultivar of *Hemerocallis:*

1. Compact, outwardly arching and clumping plant habit with upright flower scapes.
2. Freely flowering habit.

3. Pink-colored flowers with red purple-colored centers that are positioned above the foliage on strong scapes.
4. Good garden performance.

Plants of the new *Hemerocallis* differ from plants of the female parent, the cultivar Janice Brown, in the following characteristics:

1. Plants of the new *Hemerocallis* were more compact than plants of the cultivar Janice Brown.
2. Plants of the new *Hemerocallis* flower later than plants of the cultivar Janice Brown.
3. Plants of the new *Hemerocallis* and the cultivar Janice Brown differ in flower color.

Plants of the new *Hemerocallis* differ from plants of the male parent selection primarily in plant size and flower color.

Plants of the new *Hemerocallis* can be compared to plants of the cultivar Siloam Little Girl, not patented. In side-by-side comparisons conducted in Grain Valley, Mo., plants of the new *Hemerocallis* and the cultivar Siloam Little Girl differed in the following characteristics:

1. Plants of the new *Hemerocallis* had larger flowers than plants of the cultivar Siloam Little Girl.
2. Plants of the new *Hemerocallis* and the cultivar Siloam Little Girl differed in flower color.

Plants of the new *Hemerocallis* can be compared to plants of the cultivar Siloam Toy Time, not patented. In side-by-side comparisons conducted in Grain Valley, Mo., plants of the new *Hemerocallis* and the cultivar Siloam Toy Time differed in the following characteristics:

1. Plants of the new *Hemerocallis* were more compact than plants of the cultivar Siloam Toy Time.
2. Plants of the new *Hemerocallis* had larger flowers than plants of the cultivar Siloam Toy Time.
3. Plants of the new *Hemerocallis* and the cultivar Siloam Toy Time differed in flower color.

BRIEF DESCRIPTION OF THE PHOTOGRAPHS

The accompanying colored photographs illustrate the overall appearance of the new *Hemerocallis,* showing the colors as true as it is reasonably possible to obtain in colored reproductions of this type. Colors in the photographs may differ slightly from the color values cited in the detailed botanical description which accurately describes the colors of the new *Hemerocallis.*

The photograph on the first sheet comprises a side perspective view of three typical flowering plant of 'Robdayste' grown in an outdoor nursery.

The photograph on the second sheet is a close-up view of a typical flower of 'Robdayste'.

DETAILED BOTANICAL DESCRIPTION

The aforementioned photographs and following observations, measurements and values describe plants grown in Grain Valley, Mo., under commercial practice during the summer in an outdoor nursery. Plants had been growing for about two years when the photographs and description were taken. In the following description, color references are made to The Royal Horticultural Society Colour Chart, 1995 Edition, except where general terms of ordinary dictionary significance are used.

Botanical classification: *Hemerocallis hybrida* cultivar Robdayste.

Parentage:

*Female, or seed, parent.*—*Hemerocallis hybrida* cultivar Janice Brown, not patented.

*Male, or pollen, parent.*—Proprietary selection of *Hemerocallis hybrida,* not patented.

Propagation:

*Type.*—By divisions.

*Root description.*—Thick, fleshy; creamy white in color.

*Rooting habit.*—Freely branching.

Plant description:

*Plant form/habit.*—Herbaceous flowering perennial plant. Compact clumping plant habit and outwardly arching foliage with upright flower scapes. Flowering stems and leaves basal; moderately vigorous growth habit. Pink-colored flowers with red purple-colored centers positioned above the foliage on strong scapes.

*Plant height* (*soil level to top of inflorescences*).—About 55 cm.

*Plant width* (*spread*).—About 60 cm.

Foliage description:

*Arrangement/form.*—Leaves basal, simple, sessile.

*Length.*—About 65 cm.

*Width.*—About 1.3 cm.

*Shape.*—Linear; keeled.

*Apex.*—Acute.

*Base.*—Decurrent.

*Margin.*—Entire.

*Texture, upper and lower surfaces.*—Smooth, glabrous.

*Venation pattern.*—Parallel.

*Color.*—Developing and fully developed leaves, upper surface: 137A; venation, 137A. Developing and fully developed leaves, lower surface: 137A to 137B; venation, 137A to 137B.

Flower description:

*Flower type/habit.*—Numerous ephemeral single funnelform flowers with fused perianth arranged in terminal racemes on strong scapes; flowers face outward or outwardly. Perianth segments separate. Freely flowering habit; about six flowers per raceme.

*Fragrance.*—Faintly fragrant; sweet.

*Natural flowering season.*—Continuously flowering during the mid-summer in Grain Valley, Mo.

*Postproduction longevity.*—Flowers last about one or two days; flowers not persistent.

*Flower buds* (*before stage of showing color*).—Height: About 5.7 cm. Diameter: About 1.3 cm. Shape: Narrowly obovate. Color: Close to 144A.

*Inflorescence height.*—About 11 cm.

*Inflorescence diameter.*—About 17 cm.

*Flower diameter.*—About 10 cm.

*Flower depth.*—About 6 cm to 8 cm.

*Perianth.*—Arrangement: Three interior segments arranged in a single whorl surrounded by an outer whorl of three exterior segments. Size, outer perianth segments: Length: About 7.1 cm. Width: About 2.7 cm. Size, inner perianth segments: Length: About 7 cm. Width: About 4 cm. Shape, outer perianth segments: Roughly elliptic; apex, obtuse with shallow notch; base, obtuse. Shape, inner perianth segments: Broadly oblanceolate; apex, acute occasionally with shallow notch; base, obtuse. Margin, outer and inner perianth segments: Entire. Texture, outer and inner perianth segments, upper and lower surfaces: Smooth, glabrous; velvety. Color, outer perianth segments: When opening and fully opened, upper surface: Towards the apex, between 37A and 39A to 39C; central band, 53A, band about 7 mm in width; towards the base, 145A. When opening and fully opened, lower surface: Towards the apex, 9A to 9B faintly underlain with 59A; towards the base, close to 145A. Color, inner perianth segments: When opening and fully opened, upper surface: Towards the apex, between 37A and 39A to 39C; central band, 60A, band about 2.6 cm in width; towards the base, 145A. When opening and fully opened, lower surface: Towards the apex, 8B to 8C underlain with close to 60A; towards the base, close to 145A.

*Flower scapes.*—Length: About 46 cm. Diameter: About 6 mm. Angle: Erect. Strength: Strong. Texture: Smooth, glabrous. Color: Close to 146A.

*Pedicels.*—Length: About 1.6 cm. Diameter: About 3 mm. Angle: About 45° from vertical. Strength: Strong. Texture: Smooth, glabrous. Color: Close to 144A.

*Reproductive organs.*—Stamens: Quantity per flower: Typically six. Filament length: About 5.2 cm. Filament color: Towards the base, 145A; towards the apex, close to 60A. Anther shape: Elongated oblong. Anther length: About 5 mm. Anther diameter: About 2 mm. Anther color: Close to 171B. Pollen amount: Moderate. Pollen color: Close to 24A. Pistils: Quantity per flower: One. Style length: About 5.5 cm. Style color: Towards the base, 145C; towards the apex, 60A. Stigma color: Close to 145A. Ovary color: Close to 144A.

*Fruits.*—Type: Three-valved loculicidal capsule. Length: About 1.8 cm. Diameter: About 1.5 cm. Texture: Smooth, glabrous. Color: Towards the base, close to 144A; towards the apex, close to 145A.

*Seeds.*—Length: About 5 mm. Diameter: About 2 mm. Texture: Smooth, glabrous. Color: Close to 155A.

Disease/pest resistance: Plants of the new *Hemerocallis* have not been noted to be resistant to pathogens and pests common to *Hemerocallis.*

Garden performance: Plants of the new *Hemerocallis* have been observed to have good garden performance and tolerate rain, wind and high temperatures of about 43° C. Plants of the new *Hemerocallis* have been observed to be hardy to USDA Zone 5.

It is claimed:

1. A new and distinct *Hemerocallis* plant named 'Robdayste' as illustrated and described.

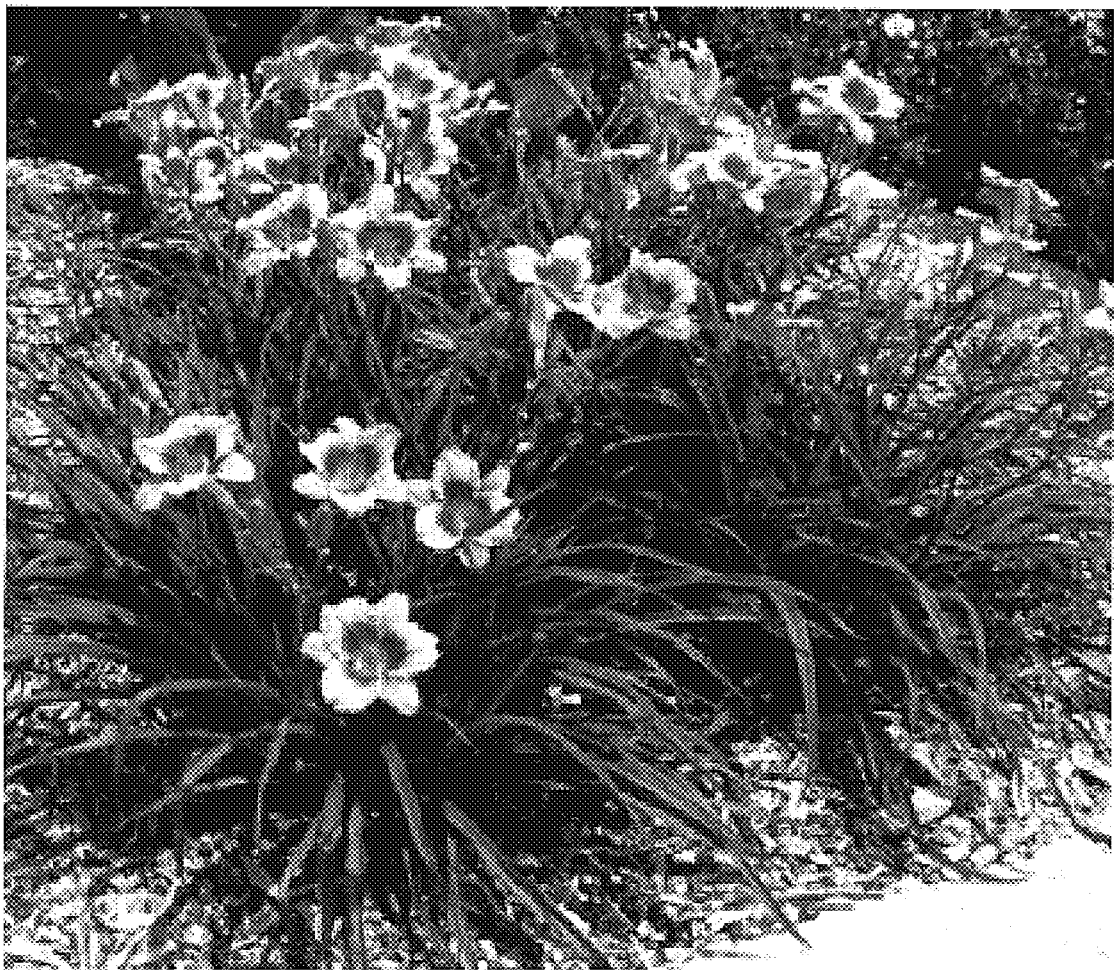

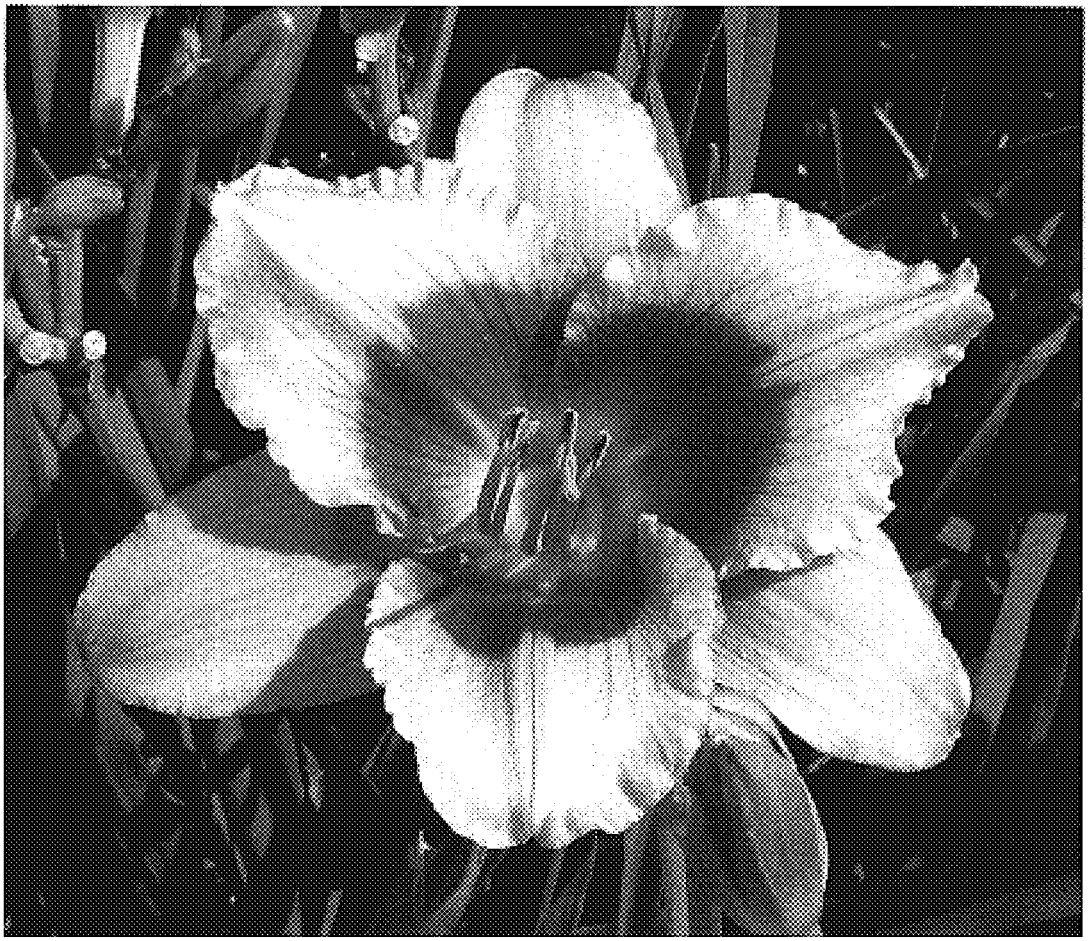

* * * * *